US010000738B2

(12) United States Patent
Wang et al.

(10) Patent No.: US 10,000,738 B2
(45) Date of Patent: Jun. 19, 2018

(54) USAGE OF ODONTOGENIC STEM CELLS AND GENETICALLY MODIFIED ODONTOGENIC STEM CELLS

(71) Applicants: Beijing Stomatology Hospital, Capital Medical University, Beijing (CN); Beijing SH Bio-Tech Corporation, Beijing (CN)

(72) Inventors: Songling Wang, Beijing (CN); Zuze Wu, Beijing (CN); Yu Cao, Beijing (CN); Hua Wang, Beijing (CN); Yi Liu, Beijing (CN); Jinsong Wang, Beijing (CN); Jingchao Hu, Beijing (CN); Jianjin Bi, Beijing (CN); Yilin Xie, Beijing (CN); Wenqiang An, Beijing (CN)

(73) Assignees: Beijing Stomatology Hospital, Capital Medical University, Beijing (CN); Beijing SH Bio-Tech Corporation, Beijing (CN)

( * ) Notice: Subject to any disclaimer, the term of this patent is extended or adjusted under 35 U.S.C. 154(b) by 0 days. days.

(21) Appl. No.: 15/114,567

(22) PCT Filed: Jan. 27, 2015

(86) PCT No.: PCT/CN2015/071589
§ 371 (c)(1),
(2) Date: Jul. 27, 2016

(87) PCT Pub. No.: WO2015/110082
PCT Pub. Date: Jul. 30, 2015

(65) Prior Publication Data
US 2016/0348076 A1    Dec. 1, 2016

(30) Foreign Application Priority Data

Jan. 27, 2014   (CN) .......................... 2014 1 0038128
Feb. 13, 2014   (CN) .......................... 2014 1 0049182

(51) Int. Cl.
| | |
|---|---|
| *C12N 5/10* | (2006.01) |
| *A61K 48/00* | (2006.01) |
| *A61K 38/18* | (2006.01) |
| *A61K 35/32* | (2015.01) |
| *C12N 5/0775* | (2010.01) |
| *C12N 5/077* | (2010.01) |

(52) U.S. Cl.
CPC ............ *C12N 5/0664* (2013.01); *A61K 35/32* (2013.01); *A61K 38/1833* (2013.01); *C12N 5/0654* (2013.01); *C12N 2510/00* (2013.01)

(58) Field of Classification Search
CPC .. C12N 5/0664; C12N 2510/00; A61K 48/00; A61K 38/1833

USPC ............................... 424/93.21; 435/366, 455
See application file for complete search history.

(56) References Cited

U.S. PATENT DOCUMENTS

2013/0195991 A1    8/2013  Ueda et al.

FOREIGN PATENT DOCUMENTS

| CN | 103037872 A | 4/2013 |
|---|---|---|
| CN | 103432007 A | 12/2013 |
| CN | 103585177 A | 2/2014 |
| WO | WO 2009/072527 A1 | 6/2009 |
| WO | WO 2010/008023 A1 | 1/2010 |
| WO | WO 2010/083730 | * 7/2010 |
| WO | WO 2010/083730 A1 | 7/2010 |
| WO | WO 2010/151733 | * 12/2010 |
| WO | WO 2010/151733 A1 | 12/2010 |

OTHER PUBLICATIONS

Nauth et al. (2012) Indian Journal of Orthopedics, vol. 46(1), 19-21.*
Wilczynska-Borawska et al. (2006) J. Oral Sci., vol. 48(2), 47-50.*
International Search Report (ISR) for PCT/CN2015/071589; I.A. fd: Jan. 27, 2015, dated Apr. 27, 2015, State Intellectual Property Office of the P.R. China, Beijing, China.
International Preliminary Report on Patentability (IPRP) including the Written Opinion of the International Searching Authority (PCT Rule 44bis) for PCT/CN2015/071589; I.A. fd: Jan. 27, 2015, dated Aug. 2, 2016, by the International Bureau of WIPO, Geneva, Switzerland.
Liu, Y et al., "Periodontal ligament stem cell-mediated treatment for periodontitis in miniature swine," Stem Cells. Apr. 2008;26(4):1065-73. doi: 10.1634/stemcells.2007-0734. Epub Jan. 31, 2008 AlphaMed Press, Dayton, OH.
D'Aquino, R et al., "Human mandible bone defect repair by the grafting of dental pulp stem/progenitor cells and collagen sponge biocomplexes," Eur Cell Mater. Nov. 12, 2009;18:75-83, AO Research Institute, Davos, Switzerland.
Ishkitiev, N et al., "High-purity hepatic lineage differentiated from dental pulp stem cells in serum-free medium," J Endod. Apr. 2012;38(4):475-80. doi: 10.1016/j.joen.2011.12.011. Epub Jan. 28, 2012 Elsevier, New York.

(Continued)

*Primary Examiner* — Anne Marie S Wehbe
(74) *Attorney, Agent, or Firm* — Sterne, Kessler, Goldstein & Fox P.L.L.C.

(57) ABSTRACT

Provided in the present invention are odontogenic stem cells and a use of genetically modified odontogenic stem cells for treating periodontal disease, repairing defects in periodontal bone tissues or soft tissues and/or promoting the regeneration of periodontal tissues, or in products for treating acute and chronic bone tissue injuries (e.g. bone fracture) or bone tissue defects. Also provided in the present invention is a composition comprising odontogenic stem cells and/or genetically modified odontogenic stem cells, wherein an exogenous hepatocyte growth factor gene is introduced into odontogenic stem cells through an adenovirus or adeno-associated virus vector to obtain the genetically modified odontogenic stem cells.

20 Claims, 6 Drawing Sheets

(56) References Cited

OTHER PUBLICATIONS

Khorsand, A et al., "Autologous dental pulp, stem cells in regeneration of defect created in canine periodontal tissue," J Oral Implantol. Aug. 2013;39(4):433-43. do: 10.1563/AAID-JOI-D-12-00027, American Academy of Implant Dentistry, Abington, MA.

Satoh E. et al., Dental Diamond 27(10): 70-75 (Aug. 2002), Dental Diamond Co., Ltd., Tokyo, Japan.

Wen, Q et al., "HGF—transgenic MSCs can improve the effects of tissue self-repair in a rabbit model of traumatic osteonecrosis of the femoral head," PLoS One, 2012;7(5):e37503. doi: 10.1371/journal.pone.0037503. Epub May 21, 2012, Public Library of Science, San Francisco, CA.

Chen, F-M et al., "Stem Cell-delivery therapeutics for periodontal tissue regeneration," Biomaterials. Jun. 2012;33:6320-44. doi: 10.1016/J.Biomaterials.2012.05.048, Elsevier Science Publishers, Barking, GB.

Inukai, T et al., "Novel application of stem-cell derived factors for periodontal regeneration," Biochemical and Biophysical Research Communications. Dec. 2012;430:763-68. doi:10.106/J.BBRC.2012.11.074, Elsevier, Amsterdam, NL.

Tsuchiya, S et al., "Osteogenic Differentiation Capacity of Porcine Dental Follicle Progenitor Cells," Connective Tissues Research. Jan. 2010;51:197-07. doi:10.3109/03008200903267542. Taylor & Francis, Milton Park, GB.

Yamada, Y et al., "Promising Cell-Based Therapy for Bone Regeneration Using Stem Cells From Deciduous Teeth, Dental Pulp, and Bone Marrow," Cell Transplantation. Nov. 2010;20:1003-13. doi:10.3727/096368910x539128. Cognizant Communication Corporation, Putnam Valley, NY.

Extended European search report including the supplementary European search report and the European search opinion, for EP Appl. No. 15 74 0673.7, dated Sep. 5, 2017, European Patent Office, Munich, Germany.

Supplementary Partial European Search Report, Lack of Unity of Invention and provisional opinion accompanying the partial search result,for EP Appl. No. 15 74 0673.7, dated May 17, 2017, European Patent Office, Munich, Germany.

* cited by examiner

CON

MSC

E-MSC

USAGE OF ODONTOGENIC STEM CELLS AND GENETICALLY MODIFIED ODONTOGENIC STEM CELLS

TECHNICAL FIELD

The present invention relates to a use of odontogenic stem cells (dental pulp stem cells, stem cells from human exfoliated deciduous teeth, periodontal ligament stem cells, stem cells from apical papilla) and genetically modified odontogenic stem cells, in particular a use of odontogenic stem cells and genetically modified odontogenic stem cells in preparation of products for treating the periodontal disease, repairing periodontal bone tissue and soft tissue defects caused by a variety of reasons (such as periodontal disease) and/or promoting the regeneration of periodontal tissue, as well as in preparation of products for treating acute and chronic bone tissue damage (e.g. bone fracture) or bone tissue defects. The present invention also relates to genetically modified odontogenic stem cells, as well as compound comprising odontogenic stem cells and/or genetically modified odontogenic stem cell.

BACKGROUND OF THE TECHNIQUE

Periodontitis is a common clinical oral disease, and it is an infected disease with characteristics periodontal tissue (including periodontal ligament, cementum, bone and gums) injuries; its main clinical manifestations are gingival inflammation and bleeding, formation of periodontal pockets, alveolar bone resorption and odontoseisis, mobility even missing. Periodontal disease is not only the main cause of odontoptosis, but also related to the occurrence of certain systemic diseases. Periodontal disease is prevalent in the population, and the prevalence rate of gingivitis in children and adolescents is up to 70%~90%, chronic periodontitis is more than 60%, invasive periodontitis is 5%~15% and periodontitis accounted for 30 to 44 percent of dental extraction. Once the destruction of periodontal attachment and alveolar bone occurred, the most ideal way is to complete the reconstruction of healthy periodontal tissues. At present, the clinical methods to treat periodontitis include: periodontal basic therapy (Dental scaling, curettage, root formation), periodontal flap surgery and the regeneration of periodontal tissue. The new research methods of the regeneration of periodontal tissue at home and abroad include: (1) guided tissue regeneration, GTR: The absorbable or non-absorbable biofilm or titanium film is placed on the periodontal tissue defect, to avoid the growth of epithelial tissue into periodontal defect. Filling materials, artificial bone, carrier or periodontal regeneration inducing factor can be implanted into the periodontal defect. (2) Periodontal tissue engineering regeneration technology, wherein the acquisition of seed cells is a hot research. Currently, it is found that the main stem cells associated with tooth includes: dental pulp stem cells (DPSC), stem cells from human exfoliated deciduous teeth (SHED), stem cells from the periodontal ligament (PDLSCs) and stem cells from dental apical papilla (SCAP). Thorough research of these cells not only has positive effect on the genesis and development of teeth, but also may find the source of dental tissue engineering seed cells.

INVENTION CONTENTS

Inventors found that different sources of odontogenic stem cells can be used to repair periodontal bone and soft tissue defect caused by a variety of reasons (such as periodontal disease) and to promote the regeneration of periodontal tissue after a lot of experiments. At the same time the inventors found different sources of odontogenic stem cells can also be used for repairing the bones other than alveolar bone, and further proved that gene modified odontogenic stem cells, especially the hepatocyte growth factor (HGF) gene modified stem cells had a better therapeutic effect.

The first aspect of the invention relates to a use of odontogenic stem cells in preparation of products for preventing and/or treating periodontal disease, repairing periodontal bone or soft tissue defect caused by periodontal disease and/or promoting the regeneration of periodontal tissue.

The second aspect of the invention relates to a use odontogenic stem cells in preparation of products for preventing and/or treating acute and chronic bone tissue damage (for example bone fracture), bone tissue defect or promoting bone tissue repair.

According to the use in the first or the second aspect of the invention, wherein the odontogenic stem cells are selected at least one, such as two, from the group consisting of dental pulp stem cells, stem cells from human exfoliated deciduous teeth, stem cells from the periodontal ligament and stem cells from dental apical papilla.

In one embodiment of the invention, the odontogenic stem cells are dental pulp stem cells.

In another embodiment of the invention, the odontogenic stem cells include dental pulp stem cells and stem cells from the periodontal ligament.

The third aspect of the invention relates to gene modified odontogenic stem cells characterized in that the odontogenic stem cells express the exogenous hepatocyte growth factor.

According to the gene modified odontogenic stem cells in any of the third aspect of the invention, wherein the odontogenic stem cells are selected at least one, such as two, from the group consisting of dental pulp stem cells, stem cells from human exfoliated deciduous teeth, stem cells from the periodontal ligament and stem cells from dental apical papilla.

In one embodiment of the invention, the odontogenic stem cells are dental pulp stem cells.

In another embodiment of the invention, the odontogenic stem cells include dental pulp stem cells and stem cells from the periodontal ligament.

According to the gene modified odontogenic stem cells in any of the third aspects of invention, wherein the odontogenic stem cells are transfected with the exogenous hepatocyte growth factor gene and express the exogenous hepatocyte growth factor.

According to the gene modified dental stem cells in any of the third aspects of invention, wherein the odontogenic stem cells are transfected with the exogenous hepatocyte growth factor gene by adenovirus or adeno-associated virus vectors.

The fourth aspect of the invention relates to a use of the odontogenic stem cells in any of the third aspects of invention in preparation of products for preventing and/or treating periodontal disease, repairing periodontal bone or soft tissue defect caused by periodontal disease and/or promoting the regeneration of periodontal tissue.

The fifth aspect of the invention relates to a use of the odontogenic stem cells in any of the third aspects of invention in preparation of products for preventing and/or treating acute and chronic bone tissue damage (for example bone fracture), bone tissue defect or promoting bone tissue repair.

The invention also relates to a composition comprising an effective amount of odontogenic stem cells and optionally pharmaceutically acceptable carrier or excipient. The composition is used to prevent and/or treat periodontal disease, repair periodontal bone or soft tissue defect caused by periodontal disease and/or promote the regeneration of periodontal tissue, or to prevent and/or treat acute and chronic bone tissue damage (for example bone fracture), bone tissue defect or promot bone tissue repair.

In one embodiment of the invention, the composition is cell suspension including odontogenic stem cells.

Preferably, the odontogenic stem cells are selected at least one, such as two from the group consisting of dental pulp stem cells stem cells from human exfoliated deciduous teeth, stem cells from the periodontal ligament and stem cells from dental apical papilla.

In one embodiment of the invention, the odontogenic stem cells are dental pulp stem cells.

In another embodiment of the invention, the odontogenic stem cells include dental pulp stem cells and stem cells from the periodontal ligament.

The invention also relates to a composition comprising an effective amount of the odontogenic stem cells in the third aspect of invention and optionally pharmaceutically acceptable carrier or excipient.

In the invention of embodiment, the composition is cell suspension including the odontogenic stem cells in the third aspect the invention.

The invention also relates to a use the composition of the invention in preparation of products for preventing and/or treating periodontal disease, repairing periodontal bone or soft tissue defect caused by periodontal disease and/or promoting the regeneration of periodontal tissue.

The invention also relates to a use of the composition of the invention in preparation of products for preventing and/or treating acute and chronic bone tissue damage (for example bone fracture), bone tissue defect or promoting bone tissue repair.

The invention also relates to a use of the hepatocyte growth factor in preparation of products for preventing and/or treating periodontal disease, repairing periodontal bone or soft tissue defect caused by periodontal disease and/or promoting the regeneration of periodontal tissue, or preventing and/or treating acute and chronic bone tissue damage (for example bone fracture), bone tissue defect or promoting bone tissue repair.

The invention also relates to a method for preventing and/or treating periodontal disease, repairing periodontal bone or soft tissue defect and/or promoting the regeneration of periodontal tissue, which includes administrating an effective amount of odontogenic stem cells, the gene modified odontogenic stem cells in any one of the third aspect of the invention or the compositions in any one of the invention to subjects in need thereof.

The invention also relates to a method for preventing and/or treating acute and chronic bone tissue damage, bone tissue defect or promoting bone tissue repair, which includes administrating an effective amount of odontogenic stem cells, the gene modified odontogenic stem cells in any one of the third aspect of the invention or the compositions in any one of the invention to subjects in need thereof.

In an embodiment of the present invention, wherein the odontogenic stem cells are selected at least one, such as two from the group consisting of dental pulp stem cells, stem cells from human exfoliated deciduous teeth, stem cells from the periodontal ligament and stem cells from dental apical papilla.

In one embodiment of the present invention, a cell suspension injection is used for the treatment of the above.

The invention also relates to odontogenic stem cells, which are used for preventing and/or treating periodontal disease, repairing periodontal bone or soft tissue defect and/or promoting the regeneration of periodontal tissue, or for preventing and/or treating acute and chronic bone tissue damage, bone tissue defects, or promoting bone tissue repair.

In an embodiment of the present invention, wherein the odontogenic stem cells are selected at least one, such as two from the group consisting of dental pulp stem cells, stem cells from human exfoliated deciduous teeth, stem cells from the periodontal ligament and stem cells from dental apical papilla.

The invention also relates to the odontogenic stem cells in the third aspect of the present invention, which are used for preventing and/or treating periodontal disease, repairing periodontal bone or soft tissue defect and/or promoting the regeneration of periodontal tissue, or for preventing and/or treating acute and chronic bone tissue damage, bone tissue defects, or promoting bone tissue repair.

In the embodiment of the present invention, wherein the odontogenic stem cells are selected at least one, such as two from the group consisting of dental pulp stem cells, stem cells from human exfoliated deciduous teeth, stem cells from the periodontal ligament and stem cells from dental apical papilla.

The present inventions are detailed as follows:

The invention at the first time verified the therapeutic effect of odontogenic stem cells from different sources on teeth periodontal bone and soft tissue defect and the regeneration of periodontal tissue, so the first aspect of the invention relates to a use of odontogenic stem cells in preparation of products for treating periodontal disease, repairing periodontal bone or soft tissue defect caused by periodontal disease and/or promoting the regeneration of periodontal tissue.

The invention firstly separated and cultured of odontogenic stem cells from different tissues (e.g. dental pulp, teeth periodontal membrane, apical papilla), and proved they are mesenchymal stem cells by means of surface marker detection and osteogenic and adipogenic differentiation of the obtained odontogenic stem cells. Then the obtained odontogenic stem cells were made into cell suspension, and the odontogenic stem cells from different sources were experimentally proved to have preferable therapeutic effect for treating periodontal bone tissue, soft tissue defect and the regeneration of periodontal tissue.

At the same time, the inventor also verified that in addition to the teeth periodontal bone, the odontogenic stem cells from different sources can also be used for other bone tissues damage repair. So the second aspect of the invention relates to a use of the odontogenic stem cells in preparation of products for treating acute and chronic bone tissue damage (for example bone fracture), bone tissue defect or promoting bone tissue repair.

The invention also relates to a composition comprising an effective amount of odontogenic stem cells, wherein the composition is used for treating periodontal disease, repairing periodontal bone or soft tissue defect caused by periodontal disease and/or promoting the regeneration of periodontal tissue, or for treating acute and chronic bone tissue damage (such as bone fracture), bone tissue defect or promoting bone tissue repair.

At the same time, the inventor also has found some limitations in the local administration of odontogenic stem cells for treating periodontal disease, because cells lost special culture environment after implantation in vivo, and got nutrition only through the permeation microcirculation with a range of 100-200 μm. Therefore, more than 90% of the cells died soon after a few days of the implantation due to the lack of nutrition and then the cells cannot be well perform its anti-inflammatory, anti-apoptosis, and promote proliferation and other functions.

Hepatocyte Growth Factor (HGF) is a multifunctional growth factor, which is involved in and plays a leading role in promoting angiogenesis, inhibiting fibrosis, decreasing cell apoptosis and anti-inflammation in vivo, and so on. The present inventor found that in the process of periodontal tissue repair, HGF has the following physiological functions: (1) Reducing the expression of inflammatory factors, such as soluble intercellular adhesion molecule −1 (sICAM-1); (2) Inhibiting cell apoptosis: play its anti-apoptotic effect by activating PI3K/Akt signaling pathway or SPK-S1P signaling pathway among the others; (3) Promoting angiogenesis: improving blood perfusion by promoting the proliferation of vascular endothelial cells and angiogenesis, improving the local blood supply and hypoxic occurrence. However, the structure of HGF protein is complex, and metabolized fast in vivo. In order to obtain the high concentration of HGF in the local damage area, we need to apply large dose of recombinant protein continually. Therefore, using gene therapy strategies and using odontogenic stem cells modified with recombinant adenovirus carrying HGF to treat periodontal disease or systemic other bone tissue damage have double advantages of stem cell therapy and cell growth factor therapy, which play a Synergistic effect. On the one hand, through local injection, most odontogenic stem cells store or home in the injured periodontal tissue or other bone tissues, when play the repairing effect of stem cells, at the same time, cause the local high concentration of HGF and play its biological role; in turn, the high expressed HGF can promote tooth derived stem cell survival and proliferation, which enhances odontogenic stem cells therapeutic effect.

Therefore the third aspect of the invention relates to gene modified odontogenic stem cells which are characterized in that the odontogenic stem cells express the exogenous hepatocyte growth factor. In an embodiment of the invention, the expression of the hepatocyte growth factor is secretory expression as cells secrete HGF out of cells. In embodiments of the present invention, odontogenic stem cells express the exogenous hepatocyte growth factor by means of introducing the exogenous hepatocyte growth factor gene into odontogenic stem cells, the exogenous hepatocyte growth factor is expressed.

The method of introducing the exogenous hepatocyte growth factor gene into odontogenic stem cells is a common method for introducing exogenous gene into cells and may be, for example, virus transfection, plasmid transfection and liposome transfection. In one of the invention embodiment, the method for introducing the exogenous gene into odontogenic stem cells is viral transfection, such as adenovirus or adeno-associated virus transfection. In one embodiment of the present invention, the virus is adenovirus.

In one embodiment of the present invention, the HGF is a human hepatocyte growth factor and its gene sequence is recorded by K Miyazawa, etc (Molecular cloning and sequence analysis of cDNA for human hepatocyte growth factor. Biochem Biophys Res Commun, 1989, 163(2):967-973.)

The preparation method of HGF modified odontogenic stem cells in the present invention is as follows:

Odontogenic stem cells (such as dental pulp stem cells, stem cells from human exfoliated deciduous teeth, stem cells from the periodontal ligament and stem cells from dental apical papilla) are separated and cultured. After cultured to the third generation in vitro, the odontogenic stem cells were modified with the hepatocyte growth factor (e.g., by recombinant adenovirus (AD-HGF) carrying human hepatocyte growth factor gene). 24-48 hours after modification, the cells suspension is collected for injection treatment.

Experimental results show that HGF modified odontogenic stem cells can home to local sites of damaged periodontal tissue or other bone tissues, and express HGF. HGF can not only exert anti-inflammatory, promote angiogenesis and other biological effects, but also increase survival and proliferation of the transplanted odontogenic stem cells. Odontogenic stem cells can play its role in immune regulation, and alleviate the inflammation of damaged tissue.

Under the combined action of HGF and MSC, it can effectively reduce the damage of periodontal tissues, promote the regeneration of periodontal tissues and other bone tissues, thus to achieve the purpose of treatment.

So the invention also relates to a use of the gene modified odontogenic stem cells in any one of the third aspect of this invention in preparation of products for treating periodontal disease, repairing periodontal bone or soft tissue defect caused by periodontal disease and/or promoting the regeneration of periodontal tissue, treating acute and chronic bone tissue damage (for example bone fracture), bone tissue defect or bone tissue repair.

The invention also relates to a composition, comprising an effective amount of odontogenic stem cells or the gene modified odontogenic stem cells in any one of the third aspect of this invention.

In an embodiment of the invention, the gene modified odontogenic stem cells refers to the odontogenic stem cells modified with HGF, namely the odontogenic stem cells expressing abundant HGF through the introduction of HGF gene.

In one embodiment of the present invention, the composition is used for treating periodontal disease, periodontal bone tissue and soft tissue defects caused by periodontal disease, and/or used for promoting the regeneration of periodontal tissue, or for treating acute and chronic bone tissue damage (e.g., bone fracture), bone tissue defect or promoting of bone tissue repair.

In an embodiment of the invention, the method for treating periodontal bone defect by using odontogenic stem cells or HGF modified odontogenic stem cells is:

After establishing an experimental periodontitis model in miniature swine first mandibular molarteeth, then odontogenic stem cells or HGF gene modified odontogenic stem cells suspension are injected in bone defect area. Clinical examination (including gingival sulcus bleeding index, periodontal pocket depth, and clinical attachment loss) and imaging, histology and other indicators are used to evaluate the therapeutic effect.

In an embodiment of the invention, the method for treating acute and chronic bone tissue damage, bone tissue defects, or promoting bone tissue repair by using odontogenic stem cells or HGF modified odontogenic stem cells is:

After establishing a mouse femoral shaft fracture model, odontogenic stem cells or HGF modified odontogenic stem cells in suspension are injected in fracture site, and the therapeutic effect is evaluated by image pattern analysis.

So the invention also relates to a method for treating periodontal disease, repairing periodontal bone or soft tissue defect and/or the regeneration of periodontal tissue, or treating acute and chronic bone tissue damage, bone tissue defects, promoting bone tissue repair, in which the method includes administration to subjects in need thereof a therapeutically effective amount of odontogenic stem cells or the gene modified odontogenic stem cells in any one of the third aspect of this invention. In embodiments of the present invention, the odontogenic stem cell is selected at least one, such as two from the group consisting of dental pulp stem cells, exfoliated deciduous dental pulp stem cells, periodontal ligament stem cells and apical papilla stem cells. In one embodiment of the present invention, a cell suspension injection is used in mentioned approaches.

In the invention, the denoted odontogenic stem cells belong to mesenchymal stem cells which refer to the stem cells derived from early developmental mesodermal and ectodermal stem cells, and they have the potential of multi-directional differentiation, hematopoietic support, stem cell implantation promotion, immune regulation and self-replication among the others.

They don't express the surface markers of hematopoietic stem cells such as CD14, CD31, CD34, CD45 etc. and the Leukocyte differentiation antigen HLA-DR, but express the surface markers of CD44, CD29, CD90, CD105, CD73, CD166, etc.

In the invention, the odontogenic stem cells are derived from mammals. In an embodiment of the invention, the odontogenic stem cells from mammals are selected from the group consisting of: human, pigs (for example Wuzhishan miniature pigs, Guizhou Xiang Pigs), cattle, horses, monkeys, rats, mice, guinea pigs, sheep, goats.

In the invention, the gene modified odontogenic stem cells refer to the exogenous hepatocyte growth factor gene infected odontogenic stem cells. The odontogenic stem cells express the exogenous hepatocyte growth factor gene.

In the present invention, the treating periodontal disease, repairing periodontal bone or soft tissue defect and/or promoting the regeneration of periodontal tissue, or treating acute and chronic bone tissue damage, bone tissue defects, promoting bone tissue repair refer to a treatment of an autologous or allogeneic disease or tissue regeneration.

In the invention, the periodontal disease includes gingivitis and periodontitis. The former one occurs only in gingival tissue; while the latter is chronic infectious diseases involved four periodontal support tissue (gum, periodontal membrane, alveolar bone and cementum), which often leads to periodontal support tissue inflammatory damage, and the main clinical manifestations are inflammation of the gums, bleeding, periodontal pocket formation, alveolar bone resorption, reduced alveolar bone height, tooth loose, mobile, chewing weakness, resulting in severe pulling teeth or teeth off on their own.

In the invention, the periodontal tissue refers to periodontal support tissue, including gum, periodontal membrane, alveolar bone and cementum.

In the invention, the periodontal bone tissues include alveolar bone and cementum.

In the present invention, the periodontal soft tissues include the gingival and periodontal membranes.

In the present invention, the periodontal bone tissue and soft tissue defects include bone defect and soft tissue defect caused by chronic periodontitis, invasive periodontitis, necrotizing and ulcerative periodontitis.

In the invention, the bone tissue is also known as bone, as the support system of the human body, is mainly composed of bone, periosteum and bone marrow, which according to the shape can be divided into long bones, short, flat, irregular and mixed bones.

In the invention, the bone tissue defect refers to the structural integrity of the bone is broken. In which trauma, infection, tumor, osteomyelitis surgical debridement, and various congenital diseases are major causes of bone defects.

In an embodiment of the present invention, the bone tissue damage is fracture. In the present invention, the unmodified one refers to without HGF modified, i.e., that the extraneous HGF is not transfected into the cell.

In the invention, the term "product" refers to various forms suitable for odontogenic stem cells to be used, such as drugs, compositions, pharmaceutical compositions.

In the present invention, the term "composition" has the meanings commonly understood by the technical personnel in the field and usually refers to a form used in clinics directly or indirectly (for example, a pre dilution), such as dosage form, drug dosage form, administration form, etc. In the clinical application or drug field, the term "composition" usually has the same meaning as the "pharmaceutical composition".

Actual dose level of odontogenic stem cells in the pharmaceutical compositions or compositions of the invention can be changed for effective against a specific host, patient so as to get a good treatment or prevention. Dose levels are selected according to specific stem cell activity, the route of administration, illness severity, treatment process of disease or condition, treatment or operation process of formation and repair (as well as production, regeneration and culture etc.), and the illness condition or medical history of the patient to be treated. However, the practice in this field is that the dose of stem cells and the duration of application start from lower than the level required for getting the required treatment effectiveness, gradually increase until the desired effect is obtained. Therefore, in the case of the present invention, the technical personnel in this field may based on the information provided in the present invention, such as but not limited to the above specific circumstances, determine the specific dose applied in the specific circumstances, without the need for specific qualification. In particular, it may refer to the specific amount used in the embodiments of the present invention so as to determine the amount of use in any case.

The odontogenic stem cells in the invention can be administrated alone (i.e. by original form) or in a pharmaceutical composition. The pharmaceutical composition of this invention can be formulated into a variety of appropriate dosage forms according to the route of administration. For odontogenic stem cell processed in pharmaceutical preparations, one or more physiologically acceptable carriers, contain excipients and assistant can be used. The appropriate preparation form depends on the choice of the administration route, which can be produced in accordance with the general knowledge of this field. In an embodiment plan of the invention, the odontogenic stem cells exist in the compatible medium (e.g., physiological saline as 0.9% normal saline, etc). In an embodiment of the invention, the odontogenic stem cells exist in compatible medium, and are stored at low temperatures, for example preserved in refrigeration, freezing or other conditions and optionally before use, re-dissolved into applicable formation for application in accordance with the idea of the invention.

THE BENEFICIAL EFFECT OF THE INVENTION

The inventor successfully verified the therapeutic effects of odontogenic stem cells from different sources in repairing periodontal bone tissue and soft tissue defect and other bone tissue injury, and then provided strong evidence to expand the source of seed cells. At the same time, it is proved that the therapeutic effects of the HGF gene modified odontogenic stem cells in repairing periodontal bone and soft tissue defect and other bone tissue injury is superior to simple odontogenic stem cells, which indicates that HGF and odontogenic stem cells play a synergistic role in repairing effect.

EMBODIMENTS

Figure 1:
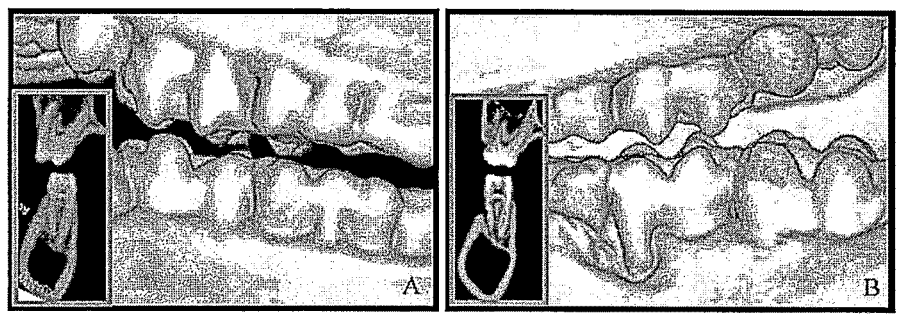
FIG. 1 Establishment of animal model for experimental periodontitis in miniature pigs. A: Teeth and its CT image before establishment of model; B: Teeth and CT images at 28 days after periodontal surgery to establish the model of periodontitis, in which it showed that the experimental periodontitis animal model is successfully established.

Carrying out plan of this invention will be described in detailed with examples below. But the technical personnel in this field will understand that the following examples are only used for the illustration of the invention, and not to be deemed to limit the scope of the invention. Conditions of more defined embodiment could be executed, in accordance with conventional conditions or manufacturers recommended ones. Reagents or instruments not indicated the manufacturer, are available through the purchase of conventional products.

The alpha MEM culture medium was purchased from American GIBCO company, the main ingredients of which are sodium pyruvate, L-valine, alanine, linoleic acid, L-arginine hydrochloride ammonia acid, ascorbic acid, L-asparagine, biotin, L-aspartic acid, D-calcium pantothenate, L-cysteine hydrochloride, folic acid, L-cysteine hydrochloride, inositol, L-glutamine, nicotinamide, L-glutamic acid, choline chloride, glycine, pyridoxinehydrochloride, L-histidine hydrochloride, riboflavin, L-isoleucine, thiamine hydrochloride, L-leucine, vitamins, L-lysine hydrochloride etc.

Example 1

Isolation, Culture, Amplification and Gene Modification of Odontogenic Stem Cells (1) Isolation and Culture of Stem Cells Use tissue culture method or enzyme digestion method to isolate pulp, periodontal ligament, apical papilla, then culture to the third generation. The odontogenic stem cells were verified as mesenchymal stem cells by cell surface marker detection and osteogenic and adipogenic differentiation. Practical isolation and culture method is following:

Isolation and culture method of periodontal ligament stem cells:

Under anesthesia, the human impacted third molar tooth was extracted or the tooth was extracted needed for orthodontic, then the new extracted teeth were placed in a centrifuge tube with sterile PBS and antibiotics immediately, and the periodontal ligament stem cells were separated within 12 hours. Peeled off periodontium gently from middle ⅓ part of dental root, washed with PBS repeatedly, cut it into pieces as possible and put in 3 mg/ml collagenase type I and 4 mg/ml Dispase solution with 37° C. water bath digestion for 0.5-1 hour, over 70 μm cell sieve, cells were collected, and then were centrifuged at 1000 rpm for 10 min, floating into single cell suspension with the right amount of medium. The cells were cultured in 10 cm culture dishes in α-MEM medium (containing 10% fetal calf serum, 2 mmol/L glutamine) and were cultured at 37° C. and 5% $CO_2$, then changed medium every 3-5 days. Cell growth status was observed under inverted microscope every day. After 1-2 weeks, the cloned cells were digested with 0.25% trypsin and passage to next generation.

Isolation and Culture Method of Dental Pulp Stem Cells:

Under anesthesia, impacted third molar tooth was extracted or the tooth was extracted needed for orthodontic, and then the new extracted teeth were placed in a centrifuge tube with sterile PBS and antibiotics immediately, and the periodontal ligament stem cells were separated within 12 hours. Obtained tooth pulp tissue after splitting crown, washed with PBS repeatedly, cut into pieces as possible and set containing 3 mg/ml collagenase type I and 4 mg/ml Dispase solution with 37⊠ water bath digestion for 0.5-1 hour, over 70 μm cell sieve, cells were collected, and then were centrifuged at 1000 rpm for 10 min, floating into single cell suspension with the right amount of medium. The cells were cultured in 10 cm culture dishes in α-MEM medium (containing 10% fetal calf serum, 2 mmol/L glutamine) and were cultured at 37⊠ and 5% $CO_2$, then changed medium every 3-5 days. Cell growth status was observed under inverted microscope every day. After 1-2 weeks, the cloned cells were digested with 0.25% trypsin and passage to next generation.

Isolation and Culture Method of Stem Cells from Dental Apical Papilla:

Anesthesia aseptic removed hypoplastic human third molar root, cut from the apical part of the apical papilla and repeatedly washed with PBS and cut it into pieces and set in 3 mg/ml collagenase type I and 4 mg/ml dispase solution and 37⊠ water bath digestion 0.5-1 hour. Over 70 μm cell sieve, cells were collected, and then were centrifuged at 1000 rpm for 10 min, floating into single cell suspension with right amount of medium. The cells were cultured in 25 $cm^2$ culture bottles in α-MEM medium (containing 15% fetal calf serum, 2 mmol/L glutamine, 100 U/ml penicillin, 100 μg/mistreptomycin) and were cultured at 37⊠ and 5% $CO_2$, then changed medium every 2-3 days. Cell growth status was observed under inverted microscope every day. When the cells grew to 80% confluence, the cloned cells were digested with 0.25% trypsin and passaged to next generation (1:2). Flow cytometry was used to detect STRO-1, CD90 and CD146 surface markers for identification of stem cells and to obtain the stem cells from apical papilla (SCAP).

The odontogenic stem cells obtained from above method of isolation and culture were tested by cell surface markers and osteogenic, adipogenic differentiation (see Perry B C, Zhou D, Wu X, Yang F C, Byers M A, Chu T M, Hockema J J, Woods E J, Goebel W S. Collection, cryopreservation, and characterization of human dental pulp-derived mesenchymal stem cells for banking and clinical use. Tissue Eng Part C Methods. 2008; 14(2): 149-156; Pittenger M F, Mackay A M, Beck S C, et al. Multilineage potential of adult human mesenchymal stem cells. Science, 1999, 284(5411): 143-147.) and verified being mesenchymal stem cells.

(2) Modification of Odontogenic Stem Cells in Vitro

Seeded 10000 odontogenic stem cells per square centimeter cultivation area, cultured for 24 hours, added 150MOI of AD-HGF (AD-HGF preparation method according to the patent "a recombinant adenovirus and its application in the treatment of myocardial ischemia, patent No. ZL 1129209.1") to the odontogenic stem cells, and get HGF gene modified odontogenic stem cells after 48 hours.

The above prepared odontogenic stem cells and in vitro modified odontogenic stem cells were used for each of the following examples.

Example 2

Therapeutic Effect of Odontogenic Stem Cells on Periodontal Bone and Soft Tissue Defect First, Wuzhishan miniature pig experimental periodontitis model was established. Then, cell suspension was injected into the periodontal bone defect site using the cell membrane implanting and cell suspension injection technology after the periodontitis models were established determined by CT imaging and clinical examination. Observed periodontal bone and soft tissue defect repairing, periodontal tissue pathological change, hematological indexes (blood routine, blood biochemical and immune globulin protein) change, and expression of inflammatory factors change respectively after 3d, 7d, 14d, 28d or 3M of treatment. Take the following dental pulp stem cells and periodontal ligament stem cells as examples to testify the treatment of odontogenic stem cells to cure periodontal bone and soft tissue defect.

(1) Establishment of Experimental Periodontitis Model in Miniature Pigs

The experimental periodontitis model was established by using the method of silk thread ligation and bone damage. 6 miniature pigs of 14 months old were selected to the control group, the dental pulp stem cells and periodontal ligament stem cell suspension injection group, and the dental pulp stem cell suspension injection group with each of 2.3 mm×5 mm×7 mm defects (FIG. 1B) were formed in the mesial surface of mandibular first molars, and then placed 4.0 silk threads in the defect site, removed them after 10 days. Clinical indicators (plaque index, gingival bleeding index, periodontal pocket depth, and clinical attachment loss) and imaging observation were performed at pre-operation, 6 weeks and 3 months post operation. From FIG. 1, it can be seen that the experimental periodontitis model of small pigs has been successfully established.

(2) Odontogenic Stem Cell Therapy for Pig Bone and Soft Tissue Defect Caused by Experimental Periodontitis $1\times10^7$ MSC cell suspension was injected to miniature swine peripheral inflammatory bone defect site 4 weeks after surgery using cell suspension injection technology, with normal saline as control. The MSC cell suspension was a mixture of dental pulp stem cells and periodontal ligament stem cells with proportion of 9:1.

(3) Results of Odontogenic Stem Cell Treatment

Figure 2:
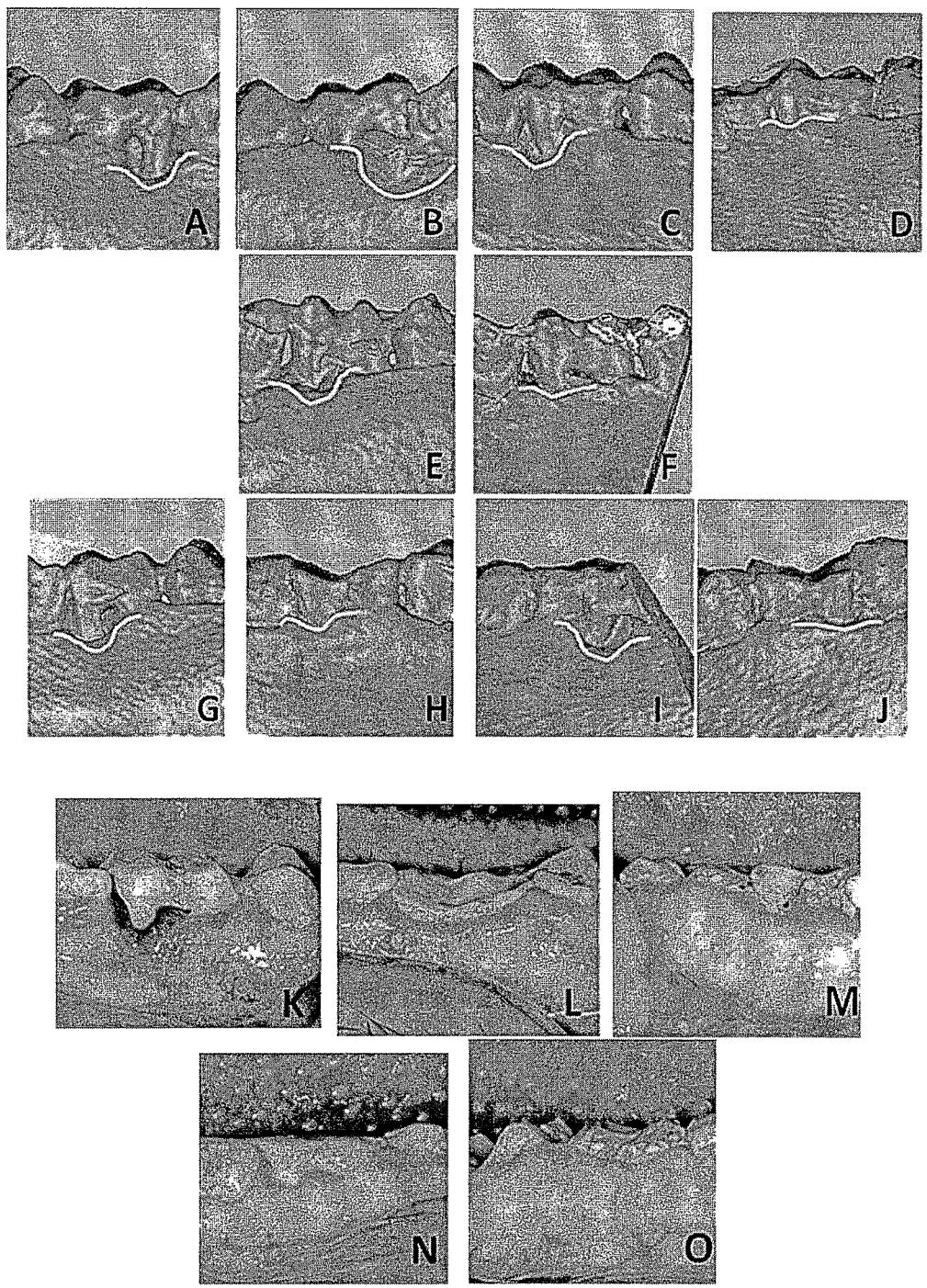
FIG. 2 Effects of odontogenic stem cells for treatment of experimental periodontitis of mini pigs. A: CT images of teeth in control group before treatment; B: CT images of teeth in control group after 3 months; C: CT images of anterior teeth before the treatment of Ad-HGF modified DPSC suspension; D: CT images of anterior teeth 3 months after the treatment of Ad-HGF modified DPSC suspension; E: CT images of anterior teeth before the treatment of DPSC suspension; F: CT images of anterior teeth 3 months after treatment of DPSC suspension; G: CT images of anterior teeth before the treatment of Ad-HGF modified DPSC+ PDLSCsuspension; H: CT images of anterior teeth 3 months after treatment of Ad-HGF modified DPSC+PDLSC suspension; I: CT images of anterior teeth before the treatment of DPSC+PDLSC suspension; J: CT images of anterior teeth 3 months after treatment of DPSC+PDLSC suspension; K: The general dental image of control group after 3 months; L: The general dental image 3 months after treatment of Ad-HGF modified DPSC suspension; M: The general dental image 3 months after treatment of DPSC suspension; N: The general dental image 3 months after treatment of Ad-HGF modified DPSC+PDLSC suspension; O: The general dental image 3 months after treatment of DPSC+PDLSC suspension.

Recovery of periodontitis bone tissue and soft tissue defect after 3 months treated with the HGF modified odontogenic stem cell suspension was significantly better than that of control group. In the first molar, the CT thin layer coronary scanning showed obvious neoformative bone image, while the control group didn't. Gross specimen showed that odontogenic stem cell treatment group of periodontal tissue is of better repair and mild gingival swelling, while control group with obvious gingival swelling and recession (such as FIG. 2-A, B, E, F, I, J, K, M, O).

Figure 3:
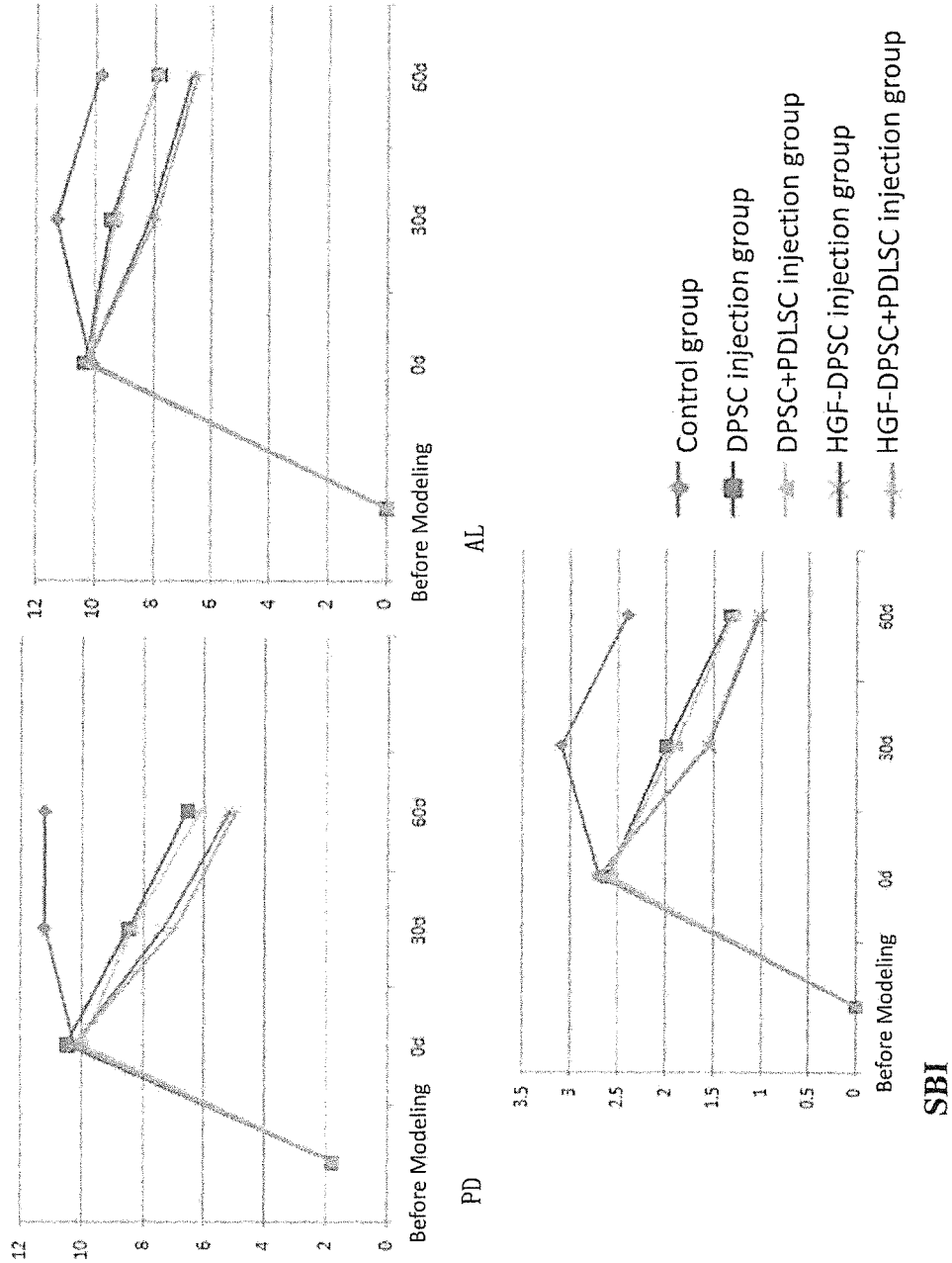
FIG. 3 Periodontal clinical attachment loss (AL), sulcus bleeding index (SBI), periodontal pocket depth (PD) in the odontogenic stem cells treatment group and the control group in the miniature pigs. The HGF-DPSC injection group indicated that the HGF modified dental pulp stem cell injection group; The DPSC injection group indicated that the non-modified dental pulp stem cell injection group; The HGF-DPSC+PDLSC injection group indicated that the HGF modified dental pulp stem cells mixed with HGF modified stem cells from the periodontal ligament injected group; The DPSC+PDLSC injection group indicated that the dental pulp stem cells mixed with stem cells from the periodontal ligament injected group; The control group was treated with saline group.

Clinical indicators (gingival sulcus bleeding index, periodontal pocket depth, and clinical attachment loss) of periodontal tissue treated with odontogenic stem cells suspension injection are better than those of the control group (FIG. 3).

Example 3

Therapeutic Effect of HGF Modified Odontogenic Stem Cell on Repairing Periodontal Bone and Soft Tissue Defect First, miniature pig experimental periodontitis model was established. Then CT imaging and clinical examination was used to confirm the establishment of periodontitis model. Cell suspension was injected into the periodontal bone defect site. Observations of periodontal bone and soft tissue defect repairing, periodontal tissue pathological change respectively were performed at 3d, 7d, 14d, 28d and 3M after treatment. Take the following HGF modified dental pulp stem cells and periodontal ligament stem cells as examples to testify the therapeutic effect of HGF modified odontogenic stem cells on periodontal bone and soft tissue defect.

(1) Establishment of Experimental Periodontitis Model in Miniature Pigs

Same as the Example 2

(2) HGF Modified Odontogenic Stem Cell Intervention in Pig Experimental Periodontitis $1 \times 10^7$ HGF modified dental pulp stem cells suspension was injected to miniature swine periodontitis bone defect site using cell suspension injection technology, with normal saline as control. Groups divided are control group, HGF modified dental pulp stem cells and periodontal ligament stem cells mixed mixture injection group (two kinds of cells are modified), HGF modified dental pulp stem cell suspension injection group, and the unmodified odontogenic stem cells treatment group. The number of dental pulp stem cells and periodontal ligament stem cells was 9:1 in the mixed cell group of dental pulp stem cells and periodontal ligament stem cells.

(3) Results of HGF Modified Odontogenic Stem Cell Treatment

Recovery of periodontitis bone tissue and soft tissue defect treated with HGF modified odontogenic stem cell was significantly better than that of the control group and non-modified cells group. In the mesial surface of the first molar, the CT thin layer coronary scanning showed obvious neo-formative bone image in the odontogenic stem cell group, non-modified group showed middle amount of new bone image, while the control group didn't. Gross specimen observation showed that HGF modified odontogenic stem cell treatment group of periodontal tissue repair is good with no gingival swelling, odontogenic stem cell treatment group is of better repair and mild gingival swelling, while control group with obvious gingival swelling and recession (such as FIG. 2-B, C, D, G, H, K, L, N).

Clinical indicators (gingival sulcus bleeding index, periodontal pocket depth, and clinical attachment loss) of periodontal tissue treated with HGF modified odontogenic stem cells suspended are better than those of the control group (FIG. 3).

Figure 4:
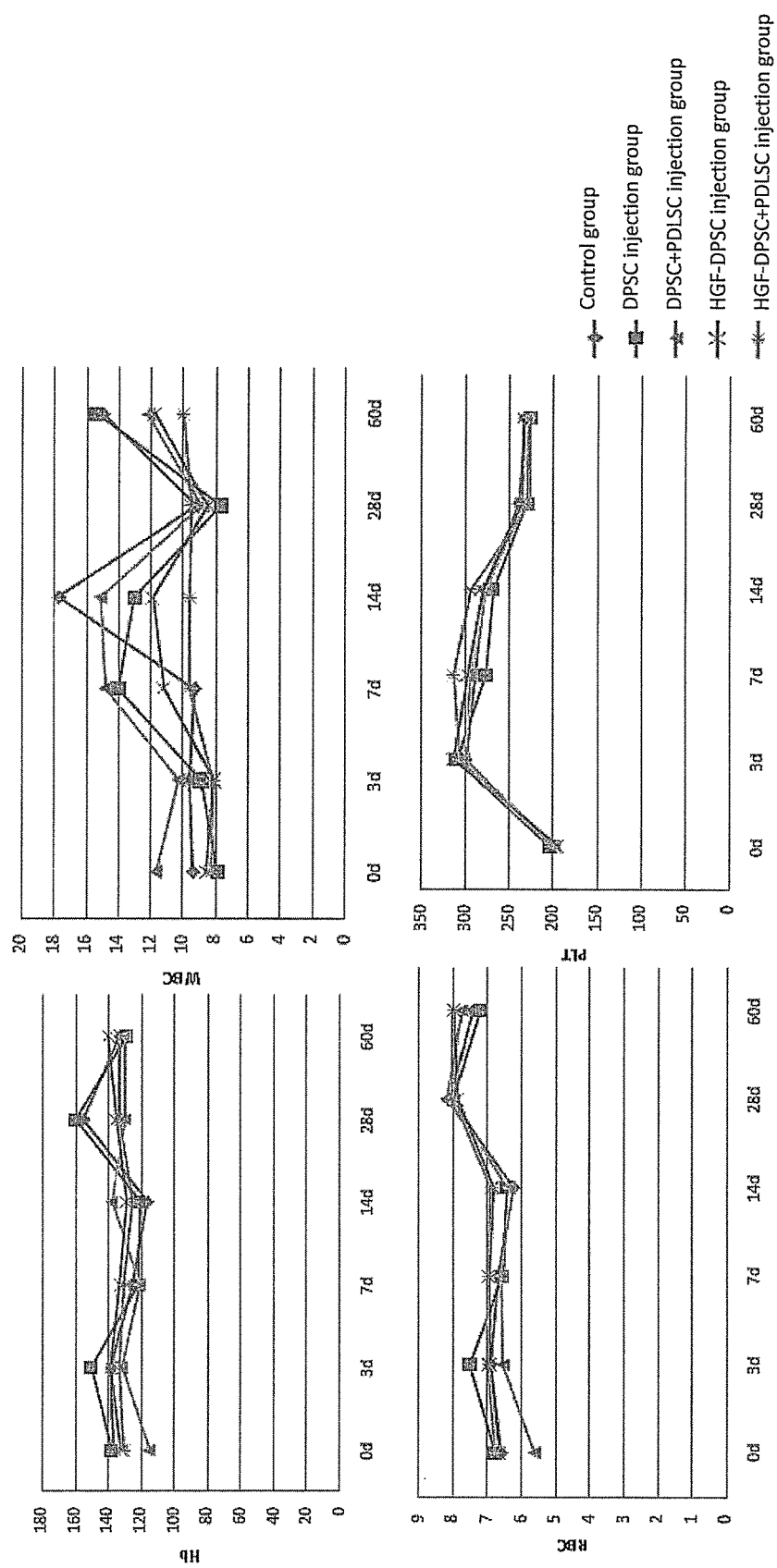
FIG. 4 The changes of hematology indexes of hemoglobin (HB), white blood cell (WBC), red blood cell (RBC), platelet (PLT) in the odontogenic stem cells treatment group and control group of miniature pigs. The HGF-DPSC injection group indicated that the HGF modified dental pulp stem cell injection group; The DPSC injection group indicated that the non-modified dental pulp stem cell injection group; The HGF-DPSC+PDLSC injection group indicated that the HGF modified dental pulp stem cells mixed with HGF modified stem cells from the periodontal ligament; The DPSC+PDLSC injection group indicated that the dental pulp stem cells mixed with stem cells from the periodontal ligament; The control group was treated with saline group.
Figure 5:
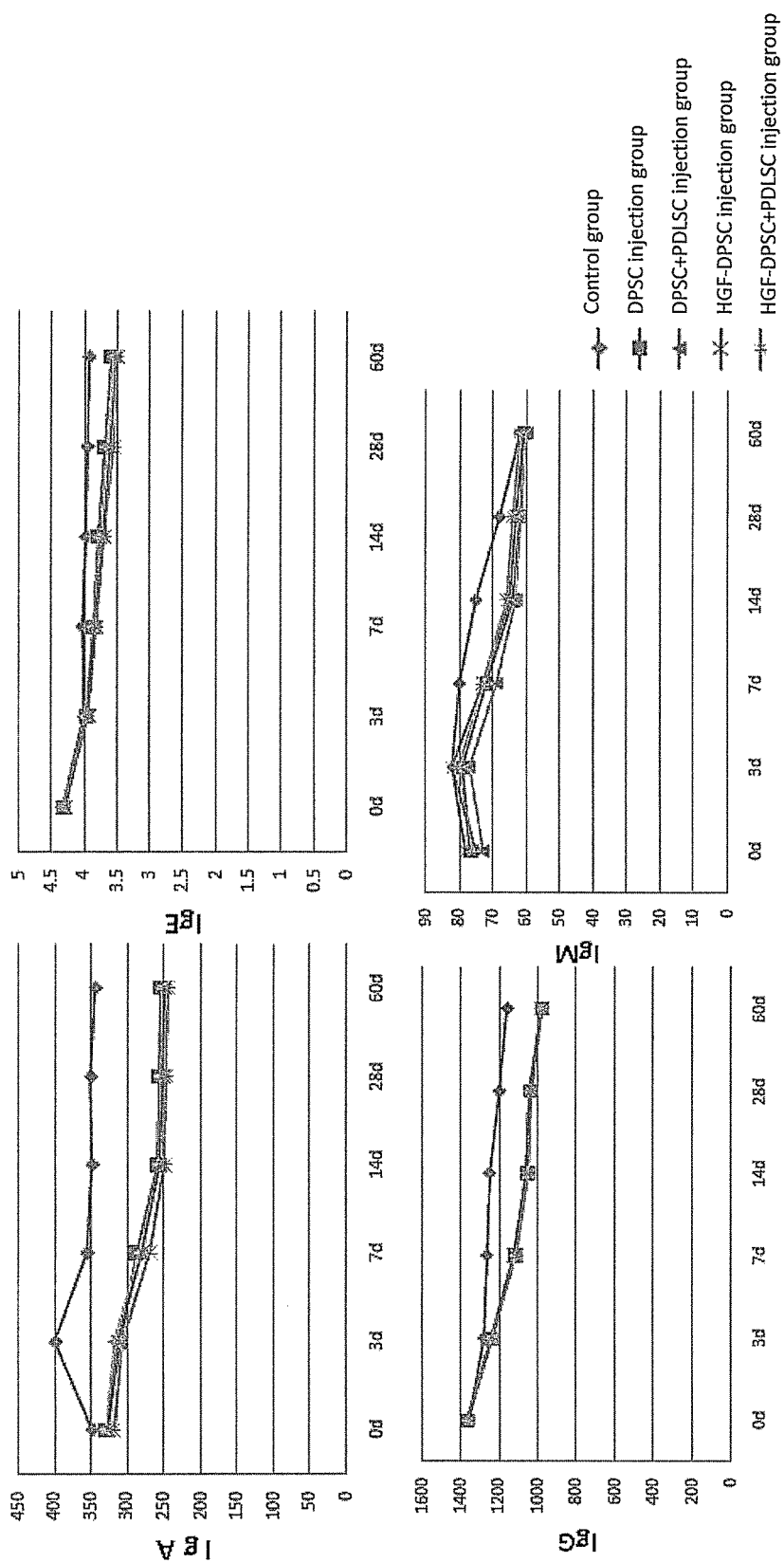
FIG. 5 The changes of blood immune index IgA, IgG, IgE, IgM in the odontogenic stem cells treatment group and control group of miniature pigs. The HGF-DPSC injection group indicated that the HGF modified dental pulp stem cell injection group; The DPSC injection group indicated that the non-modified dental pulp stem cell injection group; The HGF-DPSC+PDLSC injection group indicated that the HGF modified dental pulp stem cells mixed with HGF modified stem cells from the periodontal ligament; The DPSC+ PDLSC injection group indicated that the dental pulp stem cells mixed with stem cells from the periodontal ligament; The control group was treated with saline group.

In addition, hematological indexes (FIG. 4) and immunological detection index (FIG. 5), Local injection of HGF gene modified human odontogenic stem cells suspension did not cause significant hematological, biochemical and immunological blood changes.

Other sources of HGF modified odontogenic stem cells also have similar therapeutic effect. These results indicate that periodontal soft tissue and bone defect repair in HGF modified odontogenic stem cell treatment group is better than that of non-modified odontogenic stem cells groups. Animal inflammatory reaction of HGF modified odontogenic stem cells group better than control and unmodified odontogenic stem cells group, showed that the former has a better therapeutic effect than non-HGF modified odontogenic stem cells.

The results of clinical indicators and imaging examination showed that both unmodified human odontogenic stem cells and HGF modified odontogenic stem cells successfully repaired the periodontal bone defect and far better than blank controls in the miniature pig experimental periodontitis model.

Hematologic studies showed that both before treatment and after treatment, blood routine, biochemical, immune globulin and immunological indexes did not change significantly in every group, indicating that human odontogenic stem cell injection have no significant changes. These indicated that there were no inflammatory lesions, liver and renal damage, no recent or late humoral immune reaction and cellular immune rejection reaction. The results of the study for the human odontogenic stem cell injection in the treatment of periodontitis provide a powerful experimental basis of expanding the source of seed cells.

In summary, odontogenic stem cells have a potent therapeutic effect on the repairing periodontal bone and soft tissue defect, indicating that with odontogenic stem cells for tissue engineering of the regeneration of periodontal tissue is feasible and can have promising effect. HGF modified odontogenic stem cells can express HGF locally in the injury site of periodontal tissue and play anti-inflammatory biological effects by secreting a variety of cytokines which potentiate the effect of odontogenic stem cells in the treatment of periodontal bone defect.

Example 4

Repair of Acute Injury (Bone Fracture) of the Femur in Mice

1. Establishment of the Femoral Shaft Fracture Model in C57 Mice (5-6 Weeks)

(1) With 2.5% sodium pentobarbital in accordance with the dose of 10 mg/kg of experimental mice were intraperitoneal injection to deep anesthesia, shaved the right hind limb, fixed in supine position, with genuflex 90 degrees of right limb, iodophor disinfection, and then covered aseptic towels.

(2) On the outer side of right knee cut a longitudinal 1 cm incision to expose the distal femur and femoral quadriceps muscle tendon, pushed the femoral quadriceps muscle tendon to the inner side, fully exposed internal and external femoral intercondylar groove, a diameter of 0.45 mm stainless steel needle here was pierced into the bone marrow for internal fixation by intramedullary needle. Cut the needle handle, embedded the needle end in the skin, then closed wound.

(3) The mice were moved to collision model set of bump test table. Placed the internal fixation limb on flitch place, then take a 500 g weight from 17 cm height (proper adjustment according to mouse body type) falling down to that limb resulting femoral fracture.

(4) X-ray examination of model of fracture under anesthesia.

(5) The mice were resuscitate and moved to the animal room. At the second day, local injection of stem cells was performed.

2. Local Injection of Stem Cells (1) Mice were divided into 3 groups, 3 mice in each group: Blank control group (CON), injecting human odontogenic stem cells group (MSC group), and HGF gene modified human dental pulp stem cells group (E-MSC group).

(2) The cell concentration of MSC group and E-MSC group was $5 \times 10^5/0.4$ ml, and the blank control group was 0.9% saline.

(3) Local iodophor disinfection in the fracture site of mice.

(4) One assistant fixed the mouse, stem cells were injected into the fracture site from the middle of the femoral shaft using 1 ml syringe with 0.4 ml corresponding cell solution.

3. Observation Index of Fracture Repair

The repair of the fracture was observed under CT after two weeks of injection of stem cells.

4. Result

Figure 6:
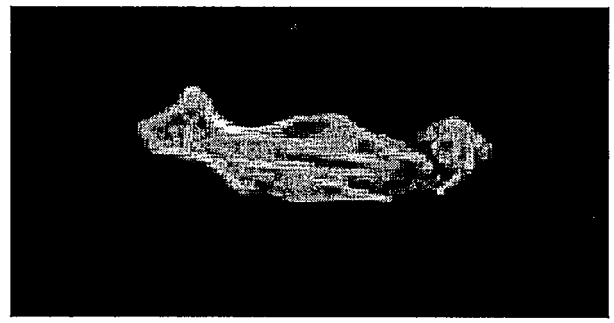
FIG. 6 CT images of 2 weeks after acute injury of the mouse femur. CON was a blank control group, MSC was the human dental pulp stem cells group, E-MSC was HGF gene modified human dental pulp stem cells.
Figure 6:
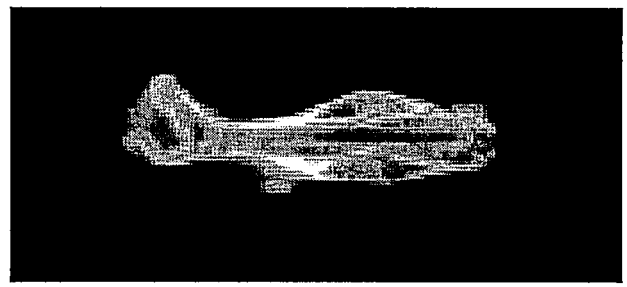
Figure 6:
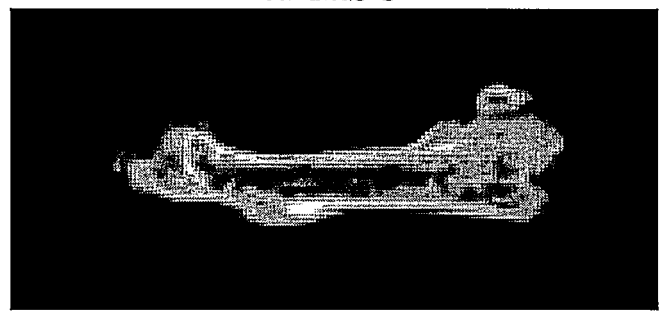

CT results see FIG. 6.

It can be seen that the control group have a large number of bone callus after two weeks, bone repair is not obvious; MSC group have a certain amount of bone callus and partial bone repair after two weeks; and the majority of bone callus has been absorbed in E-MSC group after two weeks, bone has been basically repaired.

Although the specific implementation of the invention has been described in detail, the technical personnel in this field will understand. According to all the instructions that have been publicly disclosed all these details to be changed or substituted are in the scope of protection of the invention. All the scope of the present invention is given by the appended claims and any equivalent.

The invention claimed is:

1. A method for treating bone fracture, the method comprising administering, into the bone fracture site in subjects in need thereof, a therapeutically effective amount of odontogenic stem cells that have been genetically modified to express an exogenous hepatocyte growth factor (HGF).

2. The method of claim 1, wherein the odontogenic stem cells are selected from at least one member of the group consisting of dental pulp stem cells, periodontal ligament stem cells and apical papilla stem cells.

3. The method of claim 1, wherein the odontogenic stem cells are human and the exogenous hepatocyte growth factor that is expressed is human hepatocyte growth factor.

4. The method of claim 1, wherein the genetically modified odontogenic stem cells are administered in a pharmaceutical composition that comprises the stem cells and a pharmaceutically acceptable carrier or excipient.

5. The method of claim 2, wherein the odontogenic stem cells comprise dental pulp stem cells.

6. The method of claim 5, wherein the dental pulp stem cells comprise exfoliated deciduous dental pulp stem cells.

7. The method of claim 2, wherein the odontogenic stem cells comprise periodontal ligament stem cells.

8. The method of claim 2, wherein the odontogenic stem cells comprise apical papilla stem cells.

9. The method of claim 1, wherein the administering is by injection of the cells as a cell suspension.

10. The method of claim 3, wherein the administering is by injection of the cells as a cell suspension.

11. The method of claim 4, wherein the administering is by injection of the cells as a cell suspension.

12. A method for preventing and/or treating periodontal disease, repairing periodontal bone or soft tissue defect and/or promoting the regeneration of periodontal tissue, the method comprising administering, to subjects in need thereof and at the site where the preventing, treating, repairing or promoting is to occur in the subjects, a therapeutically effective amount of odontogenic stem cells that have been genetically modified to express an exogenous hepatocyte growth factor (HGF).

13. The method of claim 12, wherein the odontogenic stem cells are selected from at least one member of the group consisting of dental pulp stem cells, periodontal ligament stem cells and apical papilla stem cells.

14. The method of claim 13, wherein the odontogenic stem cells comprise dental pulp stem cells.

15. The method of claim 14, wherein the dental pulp stem cells comprise exfoliated deciduous dental pulp stem cells.

16. The method of claim 13, wherein the odontogenic stem cells comprise periodontal ligament stem cells.

17. The method of claim 13, wherein the odontogenic stem cells comprise apical papilla stem cells.

18. The method of claim 12, wherein the genetically modified odontogenic stem cells are administered in a pharmaceutical composition that comprises the stem cells and a pharmaceutically acceptable carrier or excipient.

19. The method of claim 12, wherein the administering is by injection of the cells as a cell suspension.

20. The method of claim 12, wherein the odontogenic stem cells are human and the exogenous hepatocyte growth factor that is expressed is human hepatocyte growth factor.

* * * * *